United States Patent [19]
Keller

[11] Patent Number: 5,632,973
[45] Date of Patent: May 27, 1997

[54] ARTIFICIAL FINGERNAIL METHOD AND COMPOSITION

[76] Inventor: Alexander M. L. Keller, 130 Oxford St., Brooklyn, N.Y. 11235

[21] Appl. No.: 530,886

[22] Filed: Sep. 19, 1995

[51] Int. Cl.$^6$ .................................................. A61K 7/04
[52] U.S. Cl. ........................................ 424/61; 424/401
[58] Field of Search ......................... 424/61, 401; 132/73

[56] References Cited

U.S. PATENT DOCUMENTS

| | | | |
|---|---|---|---|
| 1,513,233 | 10/1924 | Fant | 424/61 |
| 2,633,139 | 3/1953 | Pettey | 132/73 |
| 2,688,331 | 9/1954 | Bogoslowsky | 132/73 |
| 2,746,460 | 5/1956 | Jellinek | 132/73 |
| 2,941,535 | 6/1960 | Lappe | 132/73 |
| 2,979,061 | 4/1961 | Greenman | 132/73 |
| 3,037,514 | 6/1962 | Lappe | 132/1 |
| 3,478,756 | 11/1969 | Sautter | 132/73 |
| 3,483,289 | 12/1969 | Michaelson | 424/61 |
| 3,552,401 | 1/1971 | Michaelson | 132/73 |
| 3,856,026 | 12/1974 | Gaydos | 132/73 |
| 4,007,748 | 2/1977 | Matranga | 132/73 |
| 4,070,451 | 1/1978 | Price | 424/61 |
| 4,104,333 | 8/1978 | Lee | 260/885 |
| 4,126,144 | 11/1978 | Duarte | 132/73 |
| 4,135,526 | 1/1979 | Matranga | 132/73 |
| 4,157,095 | 6/1979 | Sweet | 132/73 |
| 4,222,399 | 9/1980 | Ionescu | 132/73 |
| 4,229,431 | 10/1980 | Lee | 424/61 |
| 4,260,701 | 4/1981 | Lee | 525/303 |
| 4,273,145 | 6/1981 | Lester | 132/1 R |
| 4,299,243 | 11/1981 | Umstattd | 132/73 |
| 4,450,848 | 5/1984 | Ferrigno | 132/73 |
| 4,530,828 | 7/1985 | Smith et al. | 424/61 |
| 4,552,160 | 11/1985 | Griggs | 132/73 |
| 4,626,428 | 12/1986 | Weisberg et al. | 424/61 |
| 4,669,491 | 6/1987 | Weisberg et al. | 132/73 |
| 4,682,612 | 7/1987 | Giuliano | 132/73 |
| 4,708,866 | 11/1987 | Turco et al. | 424/61 |
| 4,745,934 | 5/1988 | Mast et al. | 132/73 |
| 4,844,102 | 7/1989 | Repensek | 132/73 |
| 4,871,534 | 10/1989 | Montgomery | 424/61 |
| 4,919,920 | 4/1990 | Devos | 424/61 |
| 5,060,678 | 10/1991 | Bauman et al. | 123/73 |
| 5,098,696 | 3/1992 | Montgomery | 424/61 |
| 5,100,674 | 3/1992 | Ser | 424/466 |
| 5,219,645 | 6/1993 | Schoon | 428/261 |
| 5,266,322 | 11/1993 | Myers | 424/401 |
| 5,330,750 | 7/1994 | Sheard | 424/61 |
| 5,346,692 | 9/1994 | Wohlrab | 424/61 |
| 5,357,985 | 10/1994 | InDelicato | 132/200 |

*Primary Examiner*—Thurman K. Page
*Assistant Examiner*—Sharon Howard
*Attorney, Agent, or Firm*—Steven Horowitz

[57] ABSTRACT

A novel composition and method for forming artificial fingernails in situ for people with weak, damaged nails. A vinyl fingernail extension is adhered to the top surface of the free end of a natural fingernail. Then a coating of cyanoacrylate adhesive is applied to the vinyl extension and the natural nail. Afterwards a layer of a pink mixture in powder form of between 8 and 12 parts by volume acrylic ester polymer or copolymer and 1 part sodium bicarbonate is applied to the adhesive coating while still wet to create an instant hardening. The coatings are repeated several times. The resulting nail looks naturally pink, blends into its finger, skin and nail environment, is hardy, corrects broken nails and is strong enough to protect against further damage to nails. The main benefit is that individuals whose nails are weak or broken and could not otherwise grow long nails because of this can do so. Also, since the vinyl absorbs the adhesive and acrylic mixture and hardens, the artificial nail of the present invention need only be reinforced approximately every four weeks, a treatment that does not involve reapplying any vinyl extension. The vinyl extension just grows off and never needs to be replaced. Other sodium compounds, namely sodium sulfate, sodium carbonate or sodium borate may be used as substitutes for sodium bicarbonate but the result will not be as good. Method also applicable to shield nails not needing an extension and to mend broken nails by applying a vinyl patch.

38 Claims, 1 Drawing Sheet

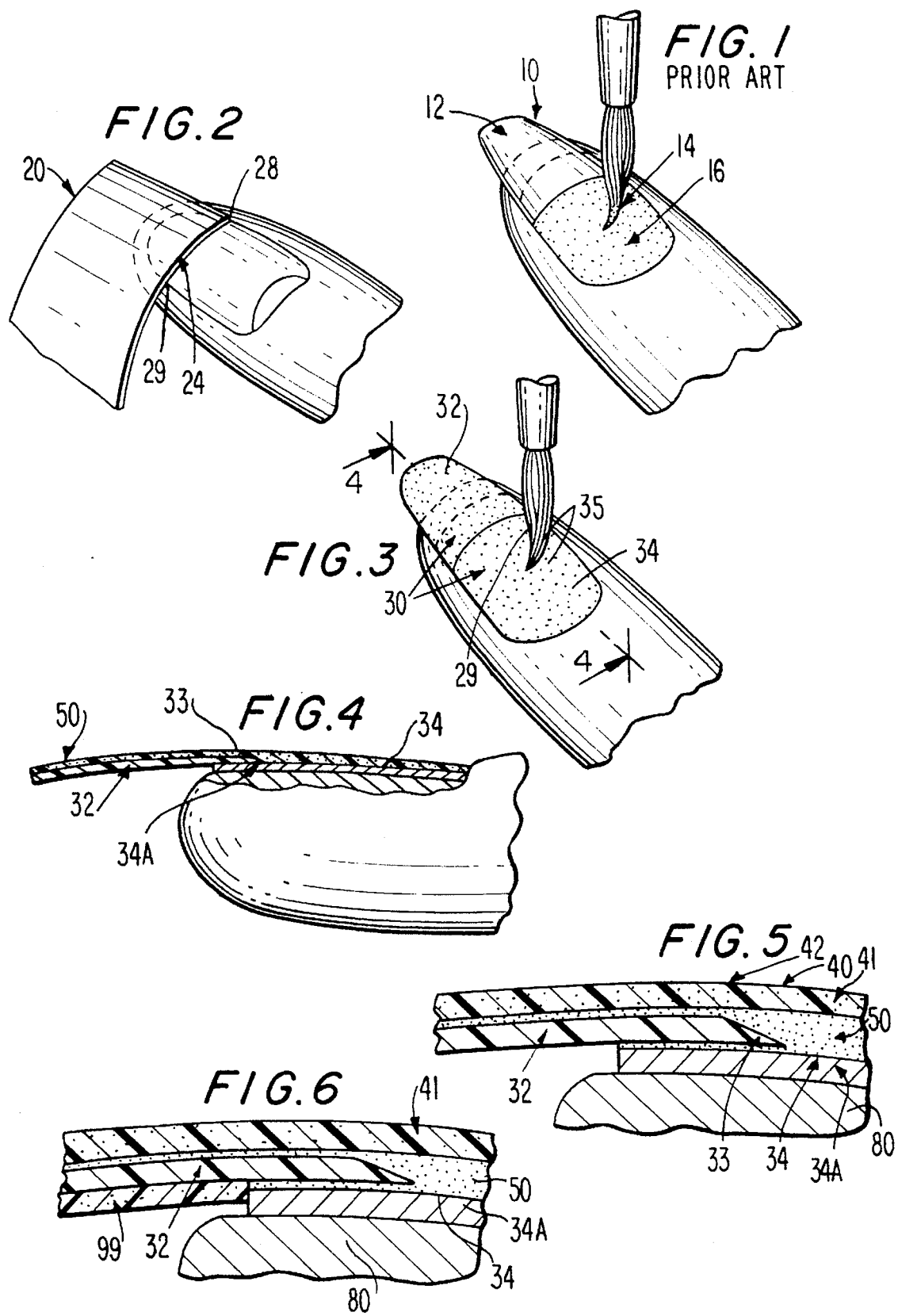

1

ARTIFICIAL FINGERNAIL METHOD AND COMPOSITION

BACKGROUND OF THE INVENTION

The present invention relates to artificial nails and in particular to a novel composition and method of forming artificial nails. Artificial nails are well known and are used mainly by women but increasingly by men also in order to beautify, correct, strengthen and protect their natural fingernails. With regard to beauty, consumers want the appearance of long, smooth, nicely shaped fingernails and any artificial nail must not only be beautiful in itself but must also create the appearance of being natural and blend effectively into its natural environment, i.e. the natural nail and finger. With regard to protecting, correcting and strengthening nails, the biggest problem is that there are many people who simply cannot grow long nails, something they want very much to do. The ideal artificial nail product would strengthen the natural nail enough to permit the wearer to grow long durable nails thereby avoiding or correcting broken or weak nails. Finally, any cosmetic product, particularly one that also has a protective function, is valuable only to the extent that it endures under normal conditions of wear and tear, does not evoke allergic reactions, is relatively easy to use and is economical.

Artificial nails of the prior art can generally be categorized into two groups: (i) preformed nails that are glued onto the natural nail and (ii) artificial nails formed on the natural fingernail by the application of a liquid solution or an adhesive composition to the natural fingernail.

The prior art contains numerous examples of prefabricated artificial nails, such as those described and claimed in U.S. Pat. Nos. 2,633,139; 2,746,460; 2,764,166; 2,941,535,; 2,979,061; 3,037,514; 3,157,912; 3,277,900; 3,425,426; 3,483,289; 3,487,831; 3,552,401 and 4,106,614. Unfortunately, preformed nails have significant disadvantages. Since they are not custom-made for every size and shaped finger, they rate poorly in terms of beauty since they do not look natural or blend effectively into their natural environment. In addition, they are not particularly effective at strengthening or protecting the nail and fall off fairly easily, thereby necessitating constant replacement. Preformed nails are often made out of hard plastic.

Accordingly, most beauty professionals employ the kind of artificial nails that are formed in situ. Even in this category, however, there are no methods or compositions that are entirely satisfactory even though it is also known in the art to apply a coating of adhesive to the top surface of a natural fingernail and to the top surface of a fingernail extension in situ. For one thing, applying this kind of artificial nail is time consuming in that one has to repeatedly visit a cosmetician and expend time while she forms the artificial nail in situ (directly on the nail). Most artificial fingernails formed in situ do not last longer than approximately one week and therefore require constant repeat visits. Furthermore, the fact that the wearer never knows when it will fall off and need immediate replacement can create embarrassment and discomfort. In addition, most artificial nails of this kind, while they look more natural than prefabricated nails, do not fully blend in with the finger and are not totally natural looking. In addition, the artificial fingernails that are formed in situ employ a form, usually plastic, around which the composition is applied and allowed to harden. The result is a less than perfect integration of the plastic form with the hardened composition and a less than perfect integration with the natural fingernail. Since the plastic form, which is usually placed on the tip of the nail, does not absorb the adhesive and is not integrated into the hardened composition to become one piece, there is no integrated whole nail created and if the plastic form comes off, the hardened composition will remain and the wearer will seem to have half a nail, or a nail of two different thicknesses. Finally, these artificial nails are not generally hard enough to adequately protect the nail from further damage or from separating and falling off the natural nail. Therefore, they do not allow the growth of long nails.

The fact of the matter is that there is great need among women and men for an artificial nail that looks natural, is hardy, strengthens and corrects broken nails and protects against further damage to nails so as to permit someone who cannot otherwise grow long beautiful nails to do so.

SUMMARY OF THE INVENTION

The primary objective of the present invention is to accomplish all of the above objectives thereby making artificial fingernails a much more valuable product. In particular, it is an object of the present invention to provide a method of forming artificial fingernails that has the pinkish color of natural nails and blends in perfectly with the natural fingernail as well as the mold used to form it.

It is an object of the present invention to provide an artificial fingernail extension made substantially of approximately 10 millimeters thick frosty clear, firm polyvinyl chloride that can absorb the cyanoacrylate adhesive mixed with the acrylic powder and hence be integrated into one piece.

It is an object of the present invention to provide a method of applying a vinyl fingernail extension that absorbs the cyanoacrylate adhesive mixed with the acrylic powder and hardens into one piece so that the vinyl extension eventually grows off and never needs to be replaced provided reinforcement treatments applying the adhesive and acrylic mixture are followed.

It is an object of the present invention to provide a method of shielding nails by applying cyanoacrylate adhesive and an acrylic powder mixture with sodium bicarbonate.

It is an object of the present invention to provide a method of mending cracked or broken nails by applying a vinyl patch over the cracked area or broken area and whereby the vinyl absorbs the cyanoacrylate adhesive and acrylic powder containing sodium bicarbonate and hardens into one piece.

It is an object of the present invention to employ a nail composition that contains a mixture of sodium bicarbonate and acrylic powder.

It is an object of the present invention to employ a nail composition that involves the procedure of adhering a vinyl fingernail extension to the top surface of a free end of the natural fingernail, applying a coating of cyanoacrylate adhesive to the top surface of both the natural nail and the vinyl extension and then applying on top of the adhesive a layer of a pink mixture in powder form of between 8 and 12 (ideally 10) parts by volume acrylic ester polymers and 1 part sodium bicarbonate to the top surface of both the natural fingernail and the vinyl extension while the adhesive coating is still wet in order to cause instant hardening.

It is a further object of the present invention to employ the above procedure using a vinyl fingernail extension that is between 8 and 12 millimeters thick, where the mixture that has between 8 and 12 parts by volume acrylic ester polymer and 1 part sodium bicarbonate has a reddening agent, the mixture is applied by spraying from a non-aerosol container, the cyanoacrylate adhesive is industrial adhesive of medium viscosity comprising ethyl cyanoacrylate and a minute amount of preservative.

It is a further object of the present invention to employ the above procedure so as to create four coatings on top and two on the underside of the nail while brushing off excess powder before each repetition and shaping and filing the resulting fingernail surface.

It is a further object of the present invention to employ the above procedure using sodium sulfate, sodium carbonate or sodium borate to be mixed with the acrylic ester polymer instead of sodium bicarbonate.

It is an object of the present invention to employ a nail composition that utilizes the composition of wherein the acrylic ester polymers powder contain benzoyl peroxide catalyst, reddening agent and opaquing agents such as titanium dioxide and silicon dioxide.

It is an object of the present invention to employ a nail composition that utilizes an industrial cyanoacrylate adhesive that is applied to the natural fingernail as well as to the vinyl extension and whereupon the acrylic powder mixture containing sodium bicarbonate is sprayed onto the entire nail.

It is an object of the present invention to employ a nail composition and method such that the wearer's natural fingernail that was weak and prone to breaking is strengthened and can grow long beautiful nails.

It is an object of the present invention to employ a nail composition and method such that the wearer's natural fingernail that was weak and prone to breaking can grow long beautiful nails requiring only reinforcement treatments every four weeks.

These and other objects of the present invention are accomplished in accordance with the method of the present invention.

THE MATERIALS—VINYL

An important novel feature of the present invention is the use of vinyl in an artificial nail composition. While prior art artificial nail compositions are made of hard plastic, silk or fiberglass, the fingernail extension of the artificial nail composition of the present invention is made of frosty clear firm vinyl. Because of the nature of vinyl it is able to absorb the cyanoacrylate adhesive and acrylic powder mixture and bond together to form hard nails.

The vinyl is typically any polyvinyl chloride compound and generally has small amounts (low parts per million) of a plasticizer and a metallic stabilizer added. The preferred color is one that is known in the industry as frosty clear or matte clear. Other colors similar to this color may also work but not as well. The thickness of the vinyl can range from 8 to 12 millimeters but 10 millimeters (i.e. 10 gauge) is ideal. The rigidity type is known in the industry as "firm". Between 3 and 8 millimeters and between 12 and 20 millimeters will also work to some extent but not the way it is supposed to. One of the advantages of vinyl as the material for the fingernail extension over acetate plastic or other hard plastic used in the prior art is that the necessary thickness of ten millimeters can be maintained while at the same time retaining the soft pliability of the vinyl. In contrast, ten millimeter plastic is hard and not very pliable. In addition, plastic that is thin enough to be soft is not thick enough to develop into hard nails as occurs with the method of the present invention.

THE ACRYLIC POWDER

The standard acrylic powder to which the sodium bicarbonate is added may be any commercially available acrylic copolymer powder composition for fingernail preparations, preferably one containing a reddening agent, and in particular an acrylic ester copolymer composition that also contains benzoyl peroxide or similar polymerization initiator. Ideally, the acrylic powder composition will also have opaquing agents such as titanium dioxide and silicon dioxide as does the Odorless Pink Powder that is commercially available from OPI Products, Inc. of North Hollywood, Calif. The purpose of the acrylic powder in the mixture of acrylic powder and sodium bicarbonate is twofold: (i) to add pink pigmentation thereby duplicating the effect of a natural nail and (ii) to avoid making the nail so hard that it is difficult to buff. The proper proportion to accomplish this is between 8 and 12 and ideally 10 parts by volume of acrylic powder to 1 part sodium bicarbonate. In other words, if the proportion of sodium bicarbonate is too high in the powder mixture, (i.e. the acrylic powder is less than 8 parts per 1 part volume sodium bicarbonate) the resulting nail will contain white spots (even if the red dye has been added to the sodium bicarbonate). If the proportion is so off that the acrylic powder is less than 1 part per 1 part sodium bicarbonate the resulting nail would also be too hard thereby making it difficult to buff. If, on the other hand, the proportion of sodium bicarbonate is too low in the powder mixture, (i.e. the acrylic powder is more than 12 parts per 1 part sodium bicarbonate) the adhesive will be aesthetically acceptable but will not instantly dry and bond with the powder and vinyl. Finally, if the proportion of sodium bicarbonate is even lower in the powder mixture, (i.e. the acrylic powder is more than 15 parts per 1 part sodium bicarbonate), the powder functions like acrylic powder without any sodium bicarbonate and dries very slowly and bonds very slowly to the vinyl.

In an alternative embodiment of the acrylic powder mixture used in the method and composition of the present invention, sodium bicarbonate may be replaced with certain other weak bases, namely sodium carbonate, sodium borate or sodium sulfate. The result will not be as good, however, aesthetically, in that the resulting nail will contain white spots as opposed to exhibiting an entirely natural and perfectly consistent light pink pigmentation. Accordingly, in this alternative embodiment, the ratio of 8 to 12 parts acrylic powder to 1 part sodium carbonate (or borate or sulfate) need not be adhered to conscientiously since the pigmentation will not be satisfactory anyway. Also, these other weak bases have larger granules and it is difficult to grind them into fine, homogeneous particles which is necessary in order to mix well with the acrylic powder.

THE NEW METHOD

In Step One of the method of the present invention, the natural fingernail is prepared for the artificial nail extension. Any dead skin around the cuticles that extend over the natural nail is removed by routine methods such as by lightly drilling the cuticle area with a small diamond bit. Then, in Step Two, cyanoacrylate adhesive is applied to the free edge of the natural fingernail by means of a nail polish brush or similar applicator enough to cover the area where the vinyl extension will be placed, namely approximately one-third of the height of the natural nail. The cyanoacrylate adhesive used is any commercially available medium viscosity (which is 20–60 cps although any viscosity between 3 and 150 cps will also work but not as well) cyanoacrylate adhesive. An example is Permabond 105 Industrial Adhesive manufactured by and available from Permabond International of Englewood, N.J. generally used for bonding to rubber and hard to bond plastics, having bond strengths of 2200–4000 psi, and made of ethyl cyanoacrylate. Permabond 105 is significantly more viscous than 5 Second Nail Glue™ or Krazy Glue™ and Permabond 105 has a roughly estimated viscosity of 30 to 40 cps at 25 degrees Centigrade/ 77 degrees Fahrenheit. An adhesive viscosity of between 20 and 60 cps is suitable for the present invention although any viscosity between 3 and 150 cps will work, although not as well. 40 cps is ideal if the container is fresh. The cyanoacrylate adhesive of the present invention also contains a minute amount of preservative which allows the bottle to last for a year. It is a colorless, transparent liquid.

In Step Three, following the application of the cyanoacrylate adhesive, a 12 inch long and ½ to ⅝ inch wide roll of the frosty clear, firm vinyl of the present invention made of polyvinyl chloride having a thickness of approximately 10 millimeters is placed on the top portion of the edge of the natural fingernail. The thickness of the vinyl can range from 8 to 12 millimeters but 10 millimeters is ideal. Between 3 and 8 and between 12 and 20 millimeters will also work to some extent but not the way it is supposed to. Using scissors, the vinyl is then cut off the roll and trimmed to fit the size of the fingernail tip. The bottom edge of the vinyl should extend over approximately one-third of the height of the natural nail. The bottom edge of the vinyl should generally correspond to an imaginary line connecting the endpoints of that section of the perimeter of the natural nail to which is attached the "whites" of the nail.

In Step Four, the bottom edge of the vinyl extension—the edge overlapping the natural nail—is then drilled with any commercially available device such as a carbide cutter or other appropriate electric nail drill with a hard bit so that there is no longer a bump on the fingernail at the beginning of the vinyl fingernail extension but rather a smooth surface at the transition point. As indicated above, the vinyl is typically any polyvinyl chloride compound with small amounts (low parts per million) of a plasticizer and a metallic stabilizer added.

Then, after dry, Step Five involves applying a first coating of cyanoacrylate adhesive on the entire nail surface (natural fingernail plus vinyl extension). Then while still wet, spray (non-aerosol) on to the entire nail surface a previously prepared mixture of standard pink acrylic powder with sodium bicarbonate having a ratio by volume of between eight (8) and twelve (12) parts (and ideally ten (10) parts) acrylic powder to 1 part sodium bicarbonate.

The application of the acrylic powder mixture will cause an instantaneous bonding and hardening between the natural nail, the polyvinyl chloride, the cyanoacrylate adhesive above and below the vinyl and the acrylic powder mixture, a hardening and bonding not achieved by the prior art. This is why the artificial fingernail extension of the present invention is made substantially of polyvinyl chloride which can absorb the compound applied on it, that is the cyanoacrylate adhesive with the acrylic powder mixture.

Step Five is repeated 3 additional times over the entire nail and 2 additional times on the underside of the vinyl extension. It should be noted that while the above number of coatings presented is ideal and recommended for the best results, the number of coatings can be lessened for people who are seeking to accomplish as much as possible but at less (labor) cost. In other words, although doing the treatment with fewer coatings will result in poorer results, the fact that the materials and methods of the present invention are utilized will still result in a better result than the prior art.

Prior to each of these 5 additional repetitions, a large cosmetic brush is used to remove excess powder, the vinyl nail extension is shaped with electric nail drills and an exceptionally rough file (e.g. cosmetic file #8080) is used to file the nail.

Step Six involves filing and buffing the nail for smoothness using known cosmetic implements. Then a final coating of the cyanoacrylate adhesive of the present invention (without the acrylic powder) is applied over the entire top surface of the nail.

The resulting nail will be smooth and natural with the same pigmentation as a natural nail. Perhaps more importantly, with the method and composition of the present invention, the wearer will achieve a clear natural look without nail polish so that a viewer cannot discern the presence of an artificial nail extension. The nail will be very hard and will be one integrated unit wherein the vinyl extension, adhesive, acrylic and natural fingernail all combine to form an integrated, strengthened aesthetically pleasing natural looking nail of beautiful shape.

If this process is followed once a month, the wearer's natural nail will have been so strengthened and, if it had gaps, filled in perfectly, that she or he will be able to grow long beautiful nails even though before beginning the treatment she could not do so because the nails were too weak to ever get long and were not hardy and beautiful.

REINFORCEMENT TREATMENTS—NO VINYL APPLIED

In order to maintain the long beautiful nails of the present invention all that is necessary is to undergo reinforcement treatments approximately once a month. In these reinforcement treatments, no vinyl extension need ever be applied. Accordingly, the vinyl extension simply grows off the nail after approximately three months (a time period which varies with each individual's nail-growing speed). In the reinforcement treatments, the first step is to shorten the nail, if necessary, by drilling the tip of the nail with an electric nail drill. In the first or second reinforcement session the tip of the nail will necessarily consist of the vinyl extension (which had been treated with the acrylic-adhesive mixture). After a few reinforcement sessions, however, each of which take place once every four weeks, the vinyl extension has grown off and the tip of the nail is the individual's natural nail with only the cyanoacrylate adhesive-acrylic powder mixture on it.

Following the drilling of the nail tip with an electric nail drill, the thickness (i.e. depth) of the nail (the part with the old coatings of adhesive-acrylic mixture), not including the natural nail that has grown in since the last session, is shaved or thinned down by an electric nail drilling. At that point, the method of the present invention used for the initial treatment session is followed so that coatings of adhesive and powder are applied to the entire nail surface (the entire surface of the natural nail plus that of any vinyl extension that remains) except that only two coatings on top and one coating on the underside of the nail are employed.

SHIELDS—NO VINYL APPLIED

Some people who have reasonably long nails and do not want a vinyl or other nail extension may obtain the benefits of the present invention without requesting a vinyl extension. Instead they would use the adhesive and powder treatment of the present invention to employ a shield on their nails. This would be done without vinyl and it would be done in almost exactly the same way the reinforcement treatments are provided. Instead of applying vinyl extension the wearer simply begins the nail treatment by applying the cyanoacrylate adhesive of the present invention followed by the acrylic powder mixture (with sodium bicarbonate) of the present invention to the entire existing natural nail. The difference between a shield and a reinforcement treatment is the number of coatings—a shield employs four coatings on the top surface of the nail and two on the bottom surface. Also, with a shield in contrast to a reinforcement treatment, the preliminary steps of shortening and drilling (before application of the adhesive) are not done.

MENDING CRACKED OR BROKEN NAILS—
VINYL PATCH

Some people who have broken or cracked nails but do not want or need a vinyl or other nail extension and cannot suffice with a shield can still obtain the benefits of the present invention by utilizing a vinyl nail patch. The method and materials associated with the vinyl nail patch are the same as the method and materials associated with the vinyl extension. The difference is only that instead of applying a "full" vinyl extension at the top of the nail (as in FIG. 2) you apply a rectangular vinyl patch large enough to surround the entire crack in the nail. The patch is cut by scissors off the same roll as the vinyl extension and same adhesive and powder are used. Since there was a crack or gap, enough adhesive is applied under the patch at the outset of the treatment to fill in the gap or crack. After the vinyl is applied, the procedure for a regular reinforcement treatment is followed except that before a first coating of adhesive is applied to the entire nail surface, you drill the edges of the vinyl patch with any commercially available device such as a carbide cutter or other appropriate electric nail drill with a hard bit so that there should no longer be a bump on the fingernail at the edges of the vinyl patch but rather a smooth surface at the transition point. This is like Step Four of the regular treatment (with vinyl extension).

BRIEF DESCRIPTION OF THE DRAWINGS

FIG. 1 is a perspective view illustrating a prior art procedure wherein the adhesive is applied rearward of the nail extension.

FIG. 2 is a plan view of a novel vinyl nail extension of the present invention applied to a fingernail.

FIG. 3 is a plan view illustrating the adhesive layer on the natural fingernail in preparation for the artificial nail employing the novel composition and method of the present invention.

FIG. 4 is a sectional elevation view taken substantially along the line 4—4 of FIG. 3 showing the nail after the cyanoacrylate adhesive has been added.

FIG. 5 is an expanded sectional view of the top part of FIG. 4 showing the hardened new nail after both the adhesive and the acrylic powder mixture have been added.

FIG. 6 is an expanded sectional view of the top part of FIG. 4 showing the hardened new nail after both the adhesive and the acrylic powder mixture have been added including on the underside of the nail extension.

DETAILED DESCRIPTION OF THE DRAWINGS

FIG. 1 depicts the prior art artificial fingernail 10 described in U.S. Pat. No. 4,450,848 to Ferrigno. In FIG. 1, a plastic extension or tip 12 is adhered to the end of the natural fingernail. FIG. 1 shows the method employed in Ferrigno whereby liquid cyanoacrylate adhesive 14 is then applied to the top surface 16 of the natural fingernail only rearward of the tip 12. Following this, a standard acrylic ester copolymer in powder form is also applied and allowed to dry. In Ferrigno, the form used on the tip (extension) is made of acetate plastic. Other methods of the prior art include the application of adhesive to the top surface of a natural fingernail and to the top surface of a fingernail extension.

FIG. 2 depicts the vinyl extension or tip 20 of the present invention. Before attaching the vinyl extension follow Step One of the method of the present invention wherein the natural fingernail is prepared for the artificial nail extension in that any dead skin around the cuticles that extend over the natural nail is removed by routine methods such as by lightly drilling the cuticle area with a small diamond bit and then, in Step Two, cyanoacrylate adhesive is applied to the free edge of the natural fingernail by means of a nail polish brush or similar applicator enough to cover the area where the vinyl extension will be placed, namely approximately one-third of the height of the natural nail.

In FIG. 2, the vinyl extension is attached to the end of the natural fingernail by placing a 12 inch long and ½ to ⅝ inch wide roll of frosty clear firm polyvinyl chloride having a thickness of approximately 10 millimeters on top of the end portion of the natural fingernail containing the adhesive. The vinyl of the present invention is a polyvinyl chloride with low amounts per million of a plasticizer and a metallic stabilizer. The thickness of the vinyl can range from 8 to 12 millimeters and 10 millimeters is ideal (although as indicated earlier 3–8 or 12–20 millimeters will work but not the way it is supposed to). Using scissors, the vinyl is then cut off the roll and trimmed to fit the size of the fingernail tip. The bottom edge of the vinyl should extend over approximately one-third of the height of the natural nail and should generally correspond to an imaginary line across the nail connecting the points 28, 29 on the perimeter of the natural nail where the "whites" of the nail end. The bottom edge 24 of the vinyl extension (the edge overlapping the natural nail) is then drilled with any commercially available device such as a carbide cutter or other appropriate electric drill with a hard bit so that there is no longer a bump on the fingernail at the beginning of the vinyl fingernail extension but rather a smooth surface at the transition point. As indicated before, one of the advantages of vinyl over acetate plastic or other hard plastic used in the prior art is that the necessary thickness of ten millimeters can be maintained while at the same time retaining the soft pliability of the vinyl. In contrast, ten millimeter plastic is hard and not very pliable. In addition, plastic that is thin enough to be soft is not thick enough to develop into hard nails in accordance with the method and composition of the present invention. FIG. 3 illustrates the application of the cyanoacrylate adhesive 35 onto the entire nail 30 including the vinyl extension 32 and the natural nail surface 34.

FIG. 4 is a sectional elevation view taken substantially along the line 4—4 of FIG. 3 after the cyanoacrylate adhesive has been added but before the acrylic powder mixture has been sprayed on with a non-aerosol spray. The adhesive layer 50 is applied on the vinyl extension 32 and on the natural nail surface 34 of natural nail 34A.

FIG. 5 is an expanded sectional view of the top part of FIG. 4 showing the hardened new nail after both the adhesive layer 50 and the acrylic powder mixture 41 have been added. As can be seen, after the application of the acrylic powder mixture the entire surface of the nail 40 is smooth and the vinyl extension, natural nail, adhesive and acrylic powder form a single integrated unit. There is no surface protrusion at the area 42 where the vinyl nail extension meets the natural nail. This is due in part to the smoothed bottom edge 33 of the vinyl extension 32 that meets the top nail surface 34 of natural fingernail 34A that sits on finger 80.

FIG. 6 is an expanded sectional view of the top part of FIG. 4 showing the hardened new nail after both the adhesive and the acrylic powder mixture have been added including a layer 99 on the underside of the nail extension 32. Natural fingernail 34A sits on finger 80.

DESCRIPTION OF EXAMPLES

The composition of the present invention will be more fully described by reference to the following examples. Parts are by weight unless otherwise specified.

EXAMPLE I

A nail composition made of a mixture of sodium bicarbonate powder and acrylic powder wherein the ratio by volume of the powder is 6 parts acrylic powder to 1 part sodium bicarbonate. The sodium bicarbonate is placed in a grinding machine and ground into a fine powder before mixing with the acrylic powder. When using other sodium compounds (sodium sulfate, sodium carbonate or sodium borate) in place of sodium bicarbonate the granules may not break up as easily into fine powder. The acrylic powder used in this mixture is as formulated as follows:

| Ingredient | Percent |
| --- | --- |
| acrylic ester copolymer | 98.7% |
| e.g. methyl methacrylate polymer | (50% of copolymer) |
| e.g. ethyl methacrylate polymer | (50% of copolymer) |
| benzoyl peroxide | approximately 1.0% |
| titanium dioxide | approximately 0.1% |
| silicon dioxide | approximately 0.1% |
| Reddening agent | approximately 0.1% |

EXAMPLE II

| Ingredient | Percent |
| --- | --- |
| acrylic ester copolymer | 98.9% |
| e.g. methyl methacrylate polymer | (70% of copolymer) |
| e.g. ethyl methacrylate polymer | (30% of copolymer) |
| benzoyl peroxide | approximately 0.8% |
| titanium dioxide | approximately 0.1% |
| silicon dioxide | approximately 0.1% |
| Reddening agent | approximately 0.1% |

In example I and II the benzoyl peroxide has varied from 0.8 to 1.0 per cent by weight of the acrylic powder and the proportion of polymers in the acrylic ester copolymer has been varied.

EXAMPLE III

A nail composition made of a mixture of sodium bicarbonate powder and acrylic powder wherein the ratio by volume of the powder is 10 parts acrylic powder to 1 part sodium bicarbonate. The sodium bicarbonate is placed in a grinding machine and ground into a fine powder to which is added 0.1% by volume reddening agent, for example D & C red dye no. 33, before mixing with the acrylic powder. When using other sodium compounds (sodium sulfate, sodium carbonate or sodium borate) in place of sodium bicarbonate the granules may not break up as easily into fine powder. The acrylic powder used in this mixture is as formulated as follows:

| Ingredient | Percent |
| --- | --- |
| acrylic ester polymers | 98.9% |
| e.g. methyl methacrylate polymer | |
| benzoyl peroxide | approximately 0.8% |
| titanium dioxide | approximately 0.1% |
| silica | approximately 0.1% |
| reddening agent | approximately 0.1% |

EXAMPLE IV

A mail composition adhesive as formulated as follows:

| Ingredient | Percent |
| --- | --- |
| ethyl cyanoacrylate | greater than 99% |
| preservative | leass than 1% |

In Examples I, II, III the benzoyl peroxide is merely illustrative of any suitable catalyst or initiator for the polymerization reaction that occurs upon adding the acrylic powder mixture to the adhesive. The titanium dioxide and the silicon dioxide (or silica) are simply opaquing agents for the powder. The reddening agent, for example D & C red dye no. 33, has been added to the acrylic powder even though the sodium bicarbonate, as explained below, contains the same reddening dye. The purpose of the reddening dye that is added to the acrylic powder is to make the sodium bicarbonate (when added to the acrylic powder) pink in a homogeneous manner, since sodium bicarbonate is naturally white. The result leaves the nails with a natural-looking pinkish pigmentation.

The acrylic ester copolymers (or polymers) are mixed together with the benzoyl peroxide, titanium dioxide, silicon dioxide and reddening dye using known standard methods of mixing such compounds such as described in standard chemistry books. Alternatively, the acrylic powder mixture (without any sodium compound) of Examples I and II can be purchased from a company such as OPI Products, Inc. of North Hollywood, Calif. already mixed. The acrylic powder mixture (without any sodium compound) of Example III can be purchased from various other companies (e.g. under the product name Nail Touch) already mixed. In either case, the following procedure at room temperature and normal pressure is used to create the final powder mixture.

The sodium bicarbonate, which comes in the form of white granules, is placed in a grinding machine or other device where it can be ground. It is then ground to fine powder. Then approximately 1 part per 5000 by volume reddening agent, such as D & C red dye no. 33, is added to the sodium bicarbonate and again mixed by the grinding machine or other mixing device in order to make the sodium bicarbonate powder slightly pink. The acrylic powder (without the sodium compound) is mixed together in a way that creates a homogeneous mixture. It is suggested, only as an example, that this can be accomplished as follows: the acrylic powder (without the sodium compound) is mixed together with the sodium bicarbonate by first scooping a predetermined volume of the acrylic powder and placing it in a container and then adding one tenth that volume of the finely ground and reddened sodium bicarbonate powder and then mixing them together with a stirring stick or grinding machine for a specified time to create one half the amount of powder desired. Then scoop out the same volume of acrylic powder as before and the same volume of sodium bicarbonate as before (maintaining the same 10 to 1 ratio) adding them to the mixture in the same order and them mixing again. It is suggested although not required that by thus first creating a mixture of half the powder amount desired and then repeating the procedure to obtain another half, that homogeneity is maximized.

Although the invention has been described in detail in the foregoing specification along with the accompanying drawing with respect to various embodiments thereof, these are intended to be illustrative only and not limiting. One skilled in the art will recognize that various modifications and variations may be made therein which are within the spirit of the invention and the scope of the appended claims.

What is claimed is:

1. A method of forming an artificial fingernail on a natural fingernail, comprising the steps of:
    a. adhering a vinyl fingernail extension to a top surface of a free end of the natural fingernail;
    b. applying a coating of cyanoacrylate adhesive to the top surface of the natural fingernail and to a top surface of the vinyl fingernail extension;
    c. applying a layer of a pink mixture in powder form of between 8 and 12 parts by volume acrylic ester polymers and 1 part sodium bicarbonate to the top surface of the natural fingernail and to the top surface of the vinyl fingernail extension on the adhesive coating while said adhesive coating is still wet to cause instant hardening;
    d. repeating steps b. and c. three times after brushing off excess powder before each repetition; and
    e. shaping and filing a resulting fingernail surface.

2. The method according to claim 1, wherein the vinyl fingernail extension is firm, is between 8 and 12 millimeters thick and is frosty clear.

3. The method according to claim 1, wherein the mixture is made of 10 parts by volume acrylic ester polymers in powder form and 1 part sodium bicarbonate in powder form.

4. The method according to claim 1, wherein the mixture is applied by spraying from a non-aerosol container.

5. The method according to claim 1, wherein steps b. and c. are repeated twice on an underside of the vinyl fingernail extension.

6. The method according to claim 1, wherein the acrylic ester copolymer powder contains a reddening agent, titanium dioxide, silicon dioxide and a peroxide catalyst.

7. The method according to claim 1, wherein a reddening agent is added to the sodium bicarbonate prior to being mixed with the acrylic ester copolymers.

8. The method according to claim 1, wherein the cyanoacrylate adhesive is industrial adhesive of medium viscosity comprising ethyl cyanoacrylate and a minute amount of preservative.

9. The method according to claim 1, wherein the vinyl fingernail extension is firm, between 8 and 12 millimeters thick and is frosty clear, the mixture has between 8 and 12 parts by volume acrylic ester polymer and 1 part sodium bicarbonate and has a reddening agent, the mixture is applied by spraying from a container, steps b. and c. are repeated twice on an underside of the vinyl fingernail extension, the cyanoacrylate adhesive is industrial adhesive of medium viscosity comprising ethyl cyanoacrylate and after step c. is completed for a first time the artificial fingernail is dried by exposure to heat.

10. The method according to claim 1, wherein the vinyl fingernail extension is firm, frosty clear and between 8 and 12 millimeters thick, the mixture has between 8 and 12 parts by volume acrylic ester polymer and 1 part sodium compound selected from the group consisting of sodium bicarbonate, sodium sulfate, sodium carbonate and sodium borate and has a reddening agent, the mixture is applied by spraying from a container, steps b. and c. are repeated twice on an underside of the vinyl fingernail extension, the cyanoacrylate adhesive is industrial adhesive of medium viscosity comprising ethyl cyanoacrylate and after step c. is completed for a first time the artificial fingernail is dried by exposure to heat.

11. A method of forming an artificial fingernail on a natural fingernail, comprising the steps of:
    a. adhering a vinyl fingernail extension to a top surface of a free end of the natural fingernail;
    b. applying a coating of cyanoacrylate adhesive to the top surface of the natural fingernail and to a top surface of the vinyl fingernail extension;
    c. applying a layer of a pink mixture in powder form of between 8 and 12 parts by volume acrylic ester polymers having a reddening agent and opaquing agents and 1 part sodium compound selected from the group consisting of sodium bicarbonate, sodium sulfate, sodium carbonate and sodium borate to the top surface of the natural fingernail and to the top surface of the vinyl fingernail extension on the adhesive coating while said adhesive coating is still wet to cause instant hardening;
    d. repeating steps b. and c. three times after brushing off excess powder before each repetition; and
    e. shaping and filing a resulting fingernail surface.

12. An artificial nail for coating human nails comprising a frosty clear vinyl fingernail extension overlapping a natural fingernail, a layer of cyanoacrylate adhesive on the vinyl fingernail extension and on the natural fingernail and a layer of a pink mixture in powder form of between 8 and 12 parts by volume acrylic ester polymers and 1 part sodium bicarbonate over the layer of cyanoacrylate adhesive.

13. The composition of claim 12, wherein the acrylic ester polymers powder contain by weight between 0.8 and 1.0% peroxide catalyst, 0.05 to 0.2% reddening agent and 0.1 to 0.3% opaquing agents.

14. The composition of claim 12, wherein the acrylic ester polymers powder contain by weight between 0.8 and 1.0% benzoyl peroxide catalyst, 0.05 to 0.2% reddening agent and 0.1 to 0.3% opaquing agents comprising titanium dioxide and silicon dioxide.

15. The composition of claim 12, wherein one member of the group selected from sodium sulfate, sodium carbonate and sodium borate replaces sodium bicarbonate.

16. The composition of claim 12, wherein the cyanoacrylate adhesive is industrial adhesive of medium viscosity comprising ethyl cyanoacrylate and a minute amount of preservative.

17. The composition of claim 12, wherein the mixture in powder form is made of 10 parts by volume acrylic ester copolymers in powder form and 1 part sodium bicarbonate in powder form.

18. The composition of claim 12, wherein the mixture in powder form is made of 10 parts by volume acrylic ester polymers in powder form and 1 part sodium bicarbonate in powder form and contains a reddening agent.

19. The composition of claim 12, wherein the vinyl fingernail extension is made of polyvinyl chloride, is frosty clear, is firm and is between 8 and 12 millimeters thick.

20. An artificial nail composition for coating a vinyl fingernail extension overlapping a natural human fingernail and for coating with it the natural human fingernail, comprising a layer of ethyl cyanoacrylate adhesive on the vinyl fingernail extension and on the natural fingernail and a layer of a pink mixture in powder form of between 8 and 12 parts by volume acrylic ester polymers and 1 part sodium bicarbonate over the layer of cyanoacrylate adhesive.

21. The composition of claim 20, wherein the acrylic ester polymers powder contain by weight between 0.8 and 1.0% peroxide catalyst, 0.05 to 0.2% reddening agent and 0.1 to 0.3% opaquing agents.

22. The composition of claim 20, wherein the acrylic ester polymers powder contain by weight between 0.8 and 1.0% benzoyl peroxide catalyst, 0.05 to 0.2% reddening agent and 0.1 to 0.3% opaquing agents comprising titanium dioxide and silicon dioxide.

23. The composition of claim 20, wherein one member of the group selected from sodium sulfate, sodium carbonate and sodium borate replaces sodium bicarbonate.

24. The composition of claim 20, wherein the cyanoacrylate adhesive is industrial adhesive of medium viscosity comprising ethyl cyanoacrylate and a minute amount of preservative.

25. The composition of claim 20, wherein the mixture in powder form is made of 10 parts by volume acrylic ester polymers in powder form and 1 part sodium bicarbonate in powder form.

26. The composition of claim 20, wherein the mixture in powder form is made of 10 parts by volume acrylic ester polymers in powder form and 1 part sodium bicarbonate in powder form and contains a reddening agent.

27. An artificial nail composition for use with human nails comprising a layer of cyanoacrylate adhesive and a layer of a pink mixture in powder form of between 8 and 12 parts by volume acrylic ester polymers powder and 1 part sodium bicarbonate powder.

28. An artificial nail composition for use with human nails comprising a layer of a pink mixture in powder form of between 8 and 12 parts by volume acrylic ester polymers powder and 1 part sodium bicarbonate powder.

29. The composition of claim 28, wherein the acrylic ester polymers powder contain by weight between 0.8 and 1.0% peroxide catalyst, 0.05 to 0.2% reddening agent and 0.1 to 0.3% opaquing agents.

30. The composition of claim 28, wherein the acrylic ester copolymers powder contain by weight between 0.8 and 1.0% benzoyl peroxide catalyst, 0.05 to 0.2% reddening agent and 0.1 to 0.3% opaquing agents comprising titanium dioxide and silicon dioxide.

31. The composition of claim 28, wherein one member of the group selected from sodium sulfate, sodium carbonate and sodium borate replaces sodium bicarbonate.

32. The composition of claim 28, wherein the cyanoacrylate adhesive is industrial adhesive of medium viscosity comprising ethyl cyanoacrylate and a minute amount of preservative.

33. The composition of claim 28, wherein the mixture in powder form is made of 10 parts by volume acrylic ester polymers in powder form and 1 part sodium bicarbonate in powder form.

34. The composition of claim 28, wherein the mixture in powder form is made of 10 parts by volume acrylic ester polymers in powder form and 1 part sodium bicarbonate in powder form and contains a reddening agent.

35. An artificial fingernail extension comprising vinyl made of polyvinyl chloride whose thickness is firm, frosty clear and between 8 and 12 millimeters thick.

36. A method of forming an artificial fingernail on a natural fingernail, comprising the steps of:

a. adhering a vinyl fingernail extension made of polyvinyl chloride whose thickness is between 8 and 12 millimeters to a top surface of a free end of the natural fingernail;

b. applying a coating of adhesive to the top surface of the natural fingernail and to a top surface of the vinyl fingernail extension;

c. applying a layer of a pink mixture in powder form of acrylic ester polymers to the top surface of the natural fingernail and to the top surface of the vinyl fingernail extension on the adhesive coating while said adhesive coating is still wet;

d. repeating steps b. and c. three times after brushing off excess powder before each repetition; and e. shaping and filing a resulting fingernail surface.

37. A method of shielding an artificial fingernail on a natural fingernail, comprising the steps of:

a. applying a coating of cyanoacrylate adhesive to the top surface of the natural fingernail;

b. applying a layer of a pink mixture in powder form of between 8 and 12 parts by volume acrylic ester polymers and 1 part sodium bicarbonate to the top surface of the natural fingernail on the adhesive coating while said adhesive coating is still wet to cause instant hardening;

d. repeating steps b. and c. three times after brushing off excess powder before each repetition; and e. shaping and filing a resulting fingernail surface.

38. A method of mending a broken natural fingernail, comprising the steps of:

a. adhering a polyvinyl chloride patch to a top surface of the natural fingernail sufficient to cover any portion of said top surface containing a break in the natural fingernail;

b. applying a coating of cyanoacrylate adhesive to the top surface of the natural fingernail and to a top surface of the polyvinyl chloride patch;

c. applying a layer of a pink mixture in powder form of between 8 and 12 parts by volume acrylic ester polymers and 1 part sodium bicarbonate to the top surface of the natural fingernail and to the top surface of the polyvinyl chloride patch on the adhesive coating while said adhesive coating is still wet to cause instant hardening;

d. repeating steps b. and c. three times after brushing off excess powder before each repetition; and e. shaping and filing a resulting fingernail surface.

* * * * *